United States Patent [19]

Tolentino

[11]  4,421,926

[45]  Dec. 20, 1983

[54] PROCESS FOR CO-ALKOXYLATION OF HALOSILANES AND SEPARATION OF THE RESULTING PRODUCTS

[75] Inventor: Luisito A. Tolentino, Ballston Lake, N.Y.

[73] Assignee: General Electric Company, Waterford, N.Y.

[21] Appl. No.: 393,011

[22] Filed: Jun. 28, 1982

[51] Int. Cl.$^3$ .......................... C07F 7/08; C07F 7/18; C07F 7/04
[52] U.S. Cl. .................................................. 556/471
[58] Field of Search ........................................ 556/471

[56] References Cited

U.S. PATENT DOCUMENTS

| | | | |
|---|---|---|---|
| 2,380,995 | 8/1945 | Rochow | 556/472 |
| 2,438,736 | 3/1948 | Barry | 556/484 |
| 2,484,394 | 10/1949 | Van Zwet | 556/471 |
| 2,485,366 | 10/1949 | DiGiorgio et al. | 556/471 |
| 2,488,487 | 11/1949 | Barry | 556/473 |
| 2,553,845 | 5/1951 | Clark | 556/471 |
| 2,701,803 | 2/1955 | Orkin | 549/4 |
| 3,008,975 | 11/1961 | Schubert | 556/417 |
| 3,448,138 | 6/1969 | DeWit | 556/471 |
| 3,651,117 | 3/1972 | Bennett | 556/417 |
| 3,792,071 | 2/1974 | Nitzsche et al. | 556/445 |
| 3,806,549 | 4/1974 | Foley | 556/446 |
| 4,039,567 | 8/1977 | Kotzsch et al. | 260/347.8 |
| 4,173,576 | 11/1979 | Seiler et al. | 556/471 |
| 4,228,092 | 10/1980 | Kotzsch et al. | 556/422 |
| 4,298,753 | 11/1981 | Schinabeck et al. | 556/415 |

*Primary Examiner*—Paul F. Shaver

[57] ABSTRACT

A process for converting a mixture of at least two different halosilanes having the general formula, $R_nSiX_{4-n}$, which are difficult to separate, to at least two different alkoxysilanes having the formula, $R_nSi(OR')_{4-n}$, where R and R' are saturated or unsaturated alkyl groups of 1 to about 8 carbon atoms or aromatic; X is halogen; and n is 0–3; and separating the alkoxysilanes, is disclosed. The co-alkoxylation of the halosilanes is carried out by charging a reboiler equipped with a reflux column with an alkoxylating agent, such as, an aliphatic alcohol, and, optionally, at least one of the halosilanes being alkoxylated; feeding at least two halosilanes to be co-alkoxylated into the upper section of the column; introducing the alkoxylating agent, such as, an aliphatic alcohol, into the upper section of the column to react with the halosilanes in a reaction zone in the column and thereby form alkoxysilanes and hydrogen halide; removing the hydrogen halide; collecting at least two alkoxysilanes formed in the column and separating the alkoxysilanes. In one preferred embodiment, the alkoxysilanes are separated and collected at two different points in the column in a distillation zone below the rection zone. Two halosilanes, which are co-methoxylated and thereafter separated, are dimethyldichlorosilane and methyltrichlorosilane which form dimethyldimethoxysilane and methyltrimethoxysilane, respectively, when heated in the presence of the alkoxylating agent, methanol.

44 Claims, No Drawings

PROCESS FOR CO-ALKOXYLATION OF HALOSILANES AND SEPARATION OF THE RESULTING PRODUCTS

BACKGROUND OF THE INVENTION

This invention relates to a process for the conversion of a mixture of halosilanes to alkoxysilanes, and more particularly, the present invention relates to a process for separating at least two alkoxysilanes prepared by the co-alkoxylation of at least two halosilanes which are difficult to separate.

The demand for alkoxysilanes, such as, dimethyldimethoxysilane and methyltrimethoxysilane, is increasing because the alkoxysilanes are now being used as important intermediates in the silicone industry for the production of various fluids and elastomers. Heretofore, it has been difficult to obtain high purity products from commercially-prepared alkoxysilanes because it is difficult to separate the halosilanes from which the alkoxysilanes are prepared. In the production of the halosilanes, it is frequently difficult and economically unfeasible to separate halosilanes, such as, dimethyldichlorosilane and methyltrichlorosilane, because of their close boiling points. Methyltrichlorosilane boils at 66° C., and dimethyldichlorosilane boils at 70° C., and when the two fractions appear in the same product in the manufacture of organosilicon halides, these close-boiling fractions are separated with difficulty in long distillation columns because of the close boiling points. For example, in the separation of dimethyldichlorosilane from methyltrichlorosilane, a very long distillation column is employed with a reflux ratio as high as 100:1. Thus, the separation of the dimethyldichlorosilane from methyltrichlorosilane is an energy intensive process.

There are many processes for preparing alkoxysilanes from halosilanes, such as, chlorosilanes, with such alkoxylating agents as hydroxyl-containing aliphatic compounds in a reflux column maintained at an elevated temperature and equipped with a reflux condenser. In certain of the prior art processes, either gaseous alcohol and gaseous chlorosilane are introduced into the column in a stoichiometric ratio from opposite points in the longitudinal sides of the column approximately one-half way up the column, or the gaseous halosilane is introduced from below into the column in counter-current flow to the alcohol, which may contain water, and which flows downward in the column.

One continuous process for preparing alkoxysilanes is described in U.S. Pat. No. 3,792,071 where chlorosilanes are reacted with optionally substituted alcohols and, if desired, water, to form polyalkoxysilanes, in a column provided with a reflux condenser and kept at an elevated temperature, wherein (a) the chlorosilane is introduced at the head of the column, and the alcohol is introduced in the gaseous form from below or at a point in the lowest one-third length of the column, and water, if used, is introduced at any desired point of the column; (b) the reaction product is removed from the column at a point below the point of introduction of the alcohol or at the lower end; (c) for at least two-thirds of the zone between the inlet of the alcohol and the inlet of the silane into the column, the column is maintained, over its entire internal cross-section at a temperature at least 0.5° C. above the boiling point of the particular alcohol at the particular pressure prevailing in the column; and (d) during the reaction excess alcohol boiling under reflux is constantly present at the head of the column.

In U.S. Pat. No. 3,651,117, halosilanes are also esterified by mixing the halosilane and a sufficient amount of alcohol in a reaction zone wherein at least 80% of the halogen groups of the halosilane are esterified by reaction with the alcohol, the reaction zone having a temperature sufficently high enough to maintain said halosilane, alcohol and the highest boiling esterified silane reaction product in the vapor state, and removing the products of the reaction from the reaction zone while in the vapor state. In U.S. Pat. No. 4,039,567, an alkoxysilane of the formula, $R_{4-n-m}Si(OR')_nCl_m$, where R is an alkyl radical or hydrogen; R' is an alkyl radical; m is 0 to 3; n is 1 to 4; and n+M is equal to or less than 4; is prepared by the esterification of a chlorosilane of the formula, $R_{4-n}SiCl_n$, with an alcohol by continuously charging liquid alcohol and liquid chlorosilane from a separate source into a distillative reaction zone having a head portion and a sump portion, maintaining the head portion at a temperature sufficient for the esterification, continuously distilling off gaseous hydrogen chloride formed during the esterification while maintaining the resultant reaction mixture in the sump at its boiling point and continuously separating liquid alkoxysilane from the sump. In another process for the esterification of an organochlorosilane by feeding alcohol into a chlorosilane maintained within a reaction zone without the alcohol contacting the chlorosilane in the gas phase wherein the esterification is performed step-wise with the extraction of hydrogen chloride which has formed as by-product, it is disclosed in U.S. Pat. No. 4,228,092, that an organochlorosilane of the formula, $R_aR_bSiCl_{4-a-b}$ wherein R is typically a halogen-substituted alkyl radical, a is 0–2, b is 1 or 2, and a+b is a maximum of 3, is employed in at least a final esterification step which is performed with the addition of heat.

Although the foregoing prior art processes are used for preparing alkoxysilanes from chlorosilanes by conventional alkoxylation, it is desirable to co-alkoxylate mixtures of halosilanes, and especially close-boiling halosilanes, to produce high purity alkoxysilanes from mixtures of halosilanes, especially for applications requiring the high purity alkoxysilane monomers. It is also desirable to eliminate the present techniques required to prepare first the high purity halosilane by energy intensive processes, such as the use of long distillation columns employing high reflux ratios, wherein the high purity alkoxysilane is prepared from a high purity halosilane.

OBJECTS OF THE INVENTION

Accordingly, it is the primary object of the present invention to provide a process for preparing high purity alkoxysilanes from a mixture of halosilanes.

It is another object of the present invention to provide a continuous process for preparing high purity alkoxysilanes from a mixture of halosilanes.

Still another object of the present invention is to provide a process for converting a mixture of at least two different halosilanes which are difficult to separate to at least two different alkoxysilanes which are less difficult to separate, and separating the at least two different alkoxysilanes.

Another object of the present invention is to provide a process for converting a mixture of halosilanes having boiling points which vary only slightly to the corresponding alkoxysilanes having boiling points which vary sufficiently, so that the alkoxysilanes are more readily separated to provide high purity alkoxysilane products.

Other objects and advantages of the present invention will become apparent when read in conjunction with the accompanying specification and claims.

SUMMARY OF THE INVENTION

The above-cited objects of the invention are accomplished by a process for converting a mixture of at least two different halosilanes having the general formula, $R_nSiX_{4-n}$, which are difficult to separate, to at least two different alkoxysilanes having the formula, $R_nSi(OR')_{4-n}$, where R and R' are selected from the group consisting of saturated or unsaturated alkyl radicals of 1 to about 8 carbon atoms, substituted saturated or unsaturated alkyl radicals of 1 to about 8 carbon atoms, cyclic carbon groups of about 4 to about 10 carbon atoms, substituted cyclic carbon groups of about 4 to about 10 carbon atoms, and excluding R', hydrogen; X is halogen; and n is 0 to 3; and separating the alkoxysilanes, comprising:

(a) charging a reboiler equipped with a column with at least one compound selected from the group consisting of an alcohol having the formula, R'OH, and, optionally, at least one halosilane having the formula, $R_nSiX_{4-n}$, or a corresponding alkoxysilane, $R_nSi(OR')_{4-n}$ where R and R' are selected from the group consisting of saturated or unsaturated alkyl radicals of 1 to about 8 carbon atoms, substituted saturated or unsaturated alkyl radicals of 1 to about 8 carbon atoms, cyclic carbon groups of about 4 to about 10 carbon atoms, substituted cyclic carbon groups of about 4 to about 10 carbon atoms, and, excluding R', hydrogen; X is halogen; and n is 0 to 3; the lower end of the column being connected to the reboiler;

(b) heating the reboiler at a temperature to cause the alcohol to reflux in the column;

(c) feeding at least two halosilanes having the formula, $R_nSiX_{4-n}$, where R, X and n are defined above, into the column;

(d) introducing an alcohol having the formula, R'OH, where R' is as defined above, into the column at a point wherein the alcohol passes into a reaction zone in the column, and the alcohol and the halosilanes react in the reaction zone to form the corresponding alkoxysilanes and hydrogen chloride;

(e) removing the hydrogen chloride;

(f) collecting at least two alkoxysilanes; and (g) separating the alkoxysilanes.

As used herein, R and R' may be any of the foregoing designated groups or radicals, or mixtures thereof, except R' cannot be hydrogen. Accordingly, R and R' are selected from the group consisting of saturated or unsaturated alkyl radicals of 1 to about 8 carbon atoms, substituted saturated or unsaturated alkyl radicals of 1 to about 8 carbon atoms, cyclic carbon groups of about 4 to about 10 carbon atoms, substituted cycli ccarbon groups of about 4 to about 10 carbon atoms, and except for R', hydrogen.

By continuously feeding a mixture of two or more of the halosilanes and an alcohol into the column, the process for converting a mixture of at least two different halosilanes to at least two different alkoxysilanes and separating the alkoxysilanes, becomes a continuous process. The process is particularly adaptable for preparing alkoxysilanes from a mixture of halosilanes which have relatively close boiling points because the corresponding alkoxysilanes generally have a greater boiling point differential. For example, methyltrichlorosilane boils at 66° C., and dimethyldichlorosilane boils at 70° C., a boiling point difference of 4° C. Dimethyldimethoxysilane has a boiling point of 82° C., and methyltrimethoxysilane has a boiling point of 102° C., a boiling point difference of 20° C. Accordingly, by co-alkoxylation, and more specifically, by co-methoxylation in preferred embodiments, the mixture of methyltrichlorosilane and dimethyldichlorosilane which are difficult to separate because of a narrow boiling point difference of 4° C., are converted to dimethyldimethoxysilane and methyltrimethoxysilane having a boiling point difference of 20° C., and therefore they are more easily separated. When alkoxysilane monomers of high purity are desired, the process of the present invention provides energy conservation in manufacturing the alkoxysilanes from mixtures of halosilanes.

The recovery of hydrogen chloride gas, for example, by means of a condenser attached to the upper section of the heated column is also possible by the process of the present invention, and the hydrogen chloride gas can be recycled and reused in various silane technologies, for example, by contacting an alkylhalide with silicon at an elevated temperature with the simultaneous introduction of hydrogen chloride along with the alkylhalide increases yields of the more valuable monoalkyl silicon halides as set forth in U.S. Pat. No. 2,488,487.

DETAILED DESCRIPTION OF THE INVENTION

The mixtures of halosilanes which may be used in the co-alkoxylation process of the present invention, are all derived from compounds of the general formula: $R_nSiX_{4-n}$ wherein R represents identical or different atoms or groups and include saturated or unsaturated alkyl radicals (straight or branched-chain) of 1 to about 8 carbon atoms, substituted saturated or unsaturated alkyl radicals (straight or branched chain) of 1 to about 8 carbon atoms wherein the substituted substituents are inert under reaction conditions, for example, halogen substituted alkyl radicals, cyclic carbon groups of about 4 to about 10 carbon atoms, for example, aryl groups, such as, phenyl and tolyl, substituted cyclic carbon groups of about 4 to about 10 carbon atoms wherein the substituted substituents are inert under reaction conditions of the present invention, hydrogen, and the like. In the above formula, n is 0 to 3; and X is a halogen, such as, chlorine, bromine, fluorine and iodine.

In most preferred embodiments, the halosilanes are chlorosilanes, and accordingly, X in the above formula is chlorine. Furthermore, in preferred embodiments, R is an alkyl group of 1 to about 4 carbon atoms, and most preferably is methyl, ethyl, propyl, isopropyl, butyl, and/or isobutyl. In the above formula, R may also be an unsaturated hydrocarbon, such as, vinyl, allyl and the like, or R may be aryl, such as, phenyl, tolyl, chlorophenyl, chlorotolyl and the like.

In preferred embodiments of the present invention, the mixtures of halosilanes are liquid, and are maintained at approximately room temperature until they enter the column. However, in certain embodiments and within the scope of the present invention, the mixture of halosilanes can also be gaseous. The halosilanes may optionally be mixed with a suitable inert solvent. Furthermore, in accordance with the present invention the mixing of halosilanes can also occur in the column, even though in preferred embodiments, the mixture of halosilanes are those which are difficult to separate and are already mixed as a result of the fact that they are products collected in the manufacture of halosilanes.

In one of the preferred embodiments of the present invention the mixture of halosilanes to be alkoxylated and thereafter separated include methyltrichlorosilane and dimethyldichlorosilane. Other examples of halosilanes which may be alkoxylated, as mixtures and separated by the process of the present invention include phenylchlorosilane, vinyltrichlorosilane, monomethyldichlorosilane, ethyltrichlorosilane, and the like.

Any alcohol operable as an alkoxylating agent may be used in the process of the present invention. The alcohol must be one which can be refluxed from the reboiler into the column connected thereto. The preferred alcohols are aliphatic alcohols. They may be substituted or unsubstituted, however, substituted substituents must be inert toward the halosilanes in the mixture of halosilanes under the particular reaction conditions. In most embodiments, the alcohols are those having the formula, R'OH where R' is a saturated or unsaturated alkyl radical (straight or branched chain) of 1 to about 8 carbon atoms, substituted saturated or unsaturated alkyl radicals (straight or branched chain) of 1 to about 8 carbon atoms, cyclic carbon groups of about 4 to about 10 carbon atoms, substituted cyclic carbon groups of about 4 to about 10 carbon atoms, and the like. The substituted alkyl may be an alkyl which is substituted, for example, by a halogen or by halogen groups, such as chlorine or fluorine. Examples of alcohols which can be employed in the process of the present invention are the aliphatic alcohols, methanol, ethanol, n-propanol, isopropanol, n-butanol, isobutanol, n-pentanol, n-hexanol, and the like, substituted aliphatic alcohols, such as, chlorobutanol, chloropropanol, fluorobutanol, and the like, unsaturated alcohols, such as alkyl alcohol, and aromatic alcohols, such as phenol, toluol, and the like. Naturally, one can utilize mixtures of alcohols for carrying out the co-alkoxylation in accordance with the process of the present invention, or one can use the alcohols in conjunction with solvents which are inert relative to the reactants.

In preferred embodiments, the alkoxylating agent, that is, the alcohol, is used in a liquid form. The alcohol must be introduced into the column separately from the mixture of halosilanes to prevent premature reactions before they are introduced into the column. In certain embodiments, the alcohol or alcohols may be introduced into the column in a gaseous form.

Alcohol is also preferably introduced into the reboiler and refluxed into the head or upper section of the column prior to start-up to establish a steady state in the column prior to the introduction of the reactants through ports in the column. In preferred embodiments, the steady state in the column is provided by refluxing the alcohol and the mixture of halosilanes and/or alkoxysilanes from the reboiler. This may also be carried out in the presence of a solvent.

As used herein, the term "gaseous" or "in the gaseous form" means that the particular component is introduced into the column as a gas or a vapor and may be introduced at temperatures at or above the boiling point of the respective component, or it may be introduced as a vapor along with an inert carrier gas.

In certain embodiments, the halosilanes and/or alcohol may be introduced into the column or reboiler in a solvent or mixture of solvents. Any suitable, inert solvent which does not interfere with the reaction or react with reactants, may be used in the process. Examples of solvents include toluene, benzene, acetone, high boiling aliphatic hydrocarbons, such as, n-hexane, n-heptane, octane, and the like.

In one preferred embodiment of the present invention, the halosilanes converted to alkoxysilanes and separated are dimethyldichlorosilane and methyltrichlorosilane. Accordingly, in accordance with at least some of the objects of the present invention, there is set forth a process for converting a mixture of dimethyldichlorosilane and methyltrichlorosilane which are difficult to separate, to dimethyldimethoxysilane and methyltrimethoxysilane by the co-methoxylation of the dimethyldichlorosilane and methyltrichlorosilane and separating the dimethyldimethoxysilane and methyltrimethoxysilane, comprising:

(a) feeding a stream of dimethyldichlorosilane and methyltrichlorosilane into a column connected to a reboiler;

(b) continuously introducing methanol into the column simultaneously with the stream of dimethyldichlorosilane and methyltrichlorosilane at a point wherein the methanol passes into a reaction zone in the column where the methanol reacts with the dimethyldichlorosilane and methyltrichlorosilane to form dimethyldimethoxysilane, methyltrimethoxysilane and hydrogen chloride in the column;

(c) heating a reboiler charged with at least one compound selected from the group consisting of methanol, dimethyldichlorosilane, dimethyldimethoxysilane, methyltrimethyoxysilane and methyltrichlorosilane, to pass the at least one compound into the column;

(d) removing hydrogen chloride from the top of the column;

(e) collecting the dimethyldimethoxysilane and methyltrimethoxysilane below the reaction zone; and (f) separating the dimethyldimethoxysilane from the methyltrimethoxysilane.

In preferred embodiments of the present invention, the mixture of dimethyldichlorosilane and methyltrichlorosilane are fed into the upper section of the heated column continuously for converting the mixture of dimethyldichlorosilane and methyltrichlorosilane which are difficult to separate, to dimethyldimethoxysilane and methyltrimethoxysilane by the co-methoxylation of the dimethyldichlorosilane and methyltrichlorosilane and separating the dimethyldimethoxysilane from the methyltrimethoxysilane in the formation of high purity products.

Since hydrogen chloride is formed in the alkoxylation steps of the present invention, the hydrogen chloride must be removed from the heated column. The hydrogen chloride may be removed by any conventional means, however, in most preferred embodiments, the hydrogen chloride is removed by a condensation scrubber attached at the exhaust end or upper section of the heated column. The hydrogen chloride gas which is removed or scrubbed from the heated column, can be recovered as by-product hydrogen chloride and used in other silicon technology. The effects of hydrogen chloride gas upon secondary reactions, and the importance of the removal of the hydrogen chloride gas are discussed in U.S. Pat. No. 4,173,576.

In accordance with the invention, the process for producing the alkoxysilanes and separating the alkoxysilanes is carried out in a column, which is preferably packed with a suitable packing material. The column is equipped with a reboiler, overhead condenser and/or a hydrogen chloride scrubber and recovery unit. Generally, the column used for the process of the invention is not critical and may be any packed column which can also be used for fractionation distillations. The condenser and/or hydrogen chloride gas scrubber provides a means for collecting or condensing and returning low boiling fractions. Low boiling contaminants and reaction by-products may be removed from the condenser and/or hydrogen chloride gas scrubber.

The alkoxysilane products form in the packed column as a result of the reaction between the mixture of halosilanes and the alkoxylating agent, such as methanol. As the alkoxysilane products form in the reaction zone of the column which generally is in the upper section of the column, for example, in the upper $\frac{2}{3}$ of the column and preferably in the upper $\frac{1}{2}$ of the column, the alkoxysilanes pass down the column to a distillation zone or collection zone located in the column below the reaction zone. Thus, the distillation or collection zone is located in the lower section of the column, for example, in the lower $\frac{1}{2}$ of the column and more preferably in the lower $\frac{1}{3}$ of the column. In the event the column is not equipped with the collection means and/or there is no provision for a distillation zone in the column, in an alternative embodiment, the alkoxysilane products pass down the column to the reboiler, and the alkoxysilane products can be continuously or intermittently drawn from the reboiler or from a collection vessel connected to the reboiler.

The reactant flow pattern and the flow pattern of the product in the reaction zone and the optional distillation or collection zone is not critical, however, there is generally an upward flow of the alcohol in the column away from the reboiler in the direction of the top of the column. As explained above, the reboiler may have connected therewith a continuous take-off system, such as a receiver for continuously removing alkoxysilane products and unreacted reactants as they enter the reboiler. In each case the flow pattern and direction of the alkoxylating agent, that is, the alcohol, the halosilanes and the alkoxysilanes depends upon boiling points of the respective compounds and the temperature of the column where the halosilanes are introduced. Furthermore, the use of a solvent may affect the flow pattern of the various components in the column. Generally, when the halosilanes are introduced into the column in the absence of alcohol refluxing therein, the halosilanes flow upward if the temperature of the column section in which they are introduced, is above the boiling point of the halosilanes and downward if the temperature of the column section in which they are introduced, is below the boiling point of the halosilanes. When alcohol is under reflux in the column when the halosilanes are fed into the column, instantaneous alkoxylation reactions occur, that is, the halosilanes are immediately converted to products, and the alkoxysilane products pass downward in the column.

The location of the point or points in the column for the introduction of the alcohol or other suitable alkoxylating agent is not critical as long as the alkoxylating agent enters the column and passes into the reaction zone, preferably in the upper $\frac{2}{3}$ of the column. In preferred embodiments, the alcohol is introduced into the heated column at a point in the column below the point of introduction of the halosilanes. In another embodiment, the alcohol is introduced into the column at a point in the column near the point of the introduction of the halosilanes. In other embodiments, especially in those embodiments wherein a continuous conversion and collection are carried out, the alcohol is introduced into the column at a plurality of points along the length of the column but preferably in the upper $\frac{2}{3}$ of the column so that there is a sufficient amount of alcohol to react with the halosilanes in the reaction zone. In most embodiments of the present invention, the alcohol is preferably maintained in about a 1:1 equimolar ratio of alcohol:halosilanes. Slight excess of alcohol, for example, up to about a 5% by weight excess of alcohol do not affect the product. Although greater excesses than 5% alcohol may be used, there is a greater risk of the formation of undesirable by-products at such greater concentrations of alcohol.

When there are a plurality of points disposed laterally in the column for the introduction of the alkoxylating agent, they are generally optimally spaced to provide the most favorable reaction conditions, and one skilled in the art can determine the best position or positions for the introduction of the alkoxylating agent to provide optimum yields or optimum high purity products. In one embodiment having a plurality of points for the introduction of the alkoxylating agent, such as methanol, the four points at which methanol are introduced into the column are spaced at intervals of about 30 cm, and the upper-most point for the introduction of the alkoxylating agent is about 7-8 cm from the top of the column. Thus, the alcohol can be introduced into the column at a plurality of points along the length of the column wherein one of the plurality of alcohol introduction points or ports is about the level of the introduction of the mixture of halosilanes, and at least one of the plurality of alcohol introduction points or ports is below the level of the introduction of the halosilanes.

As indicated above, the alkoxylating agents may be introduced into the column in either liquid form or gaseous or vapor form, and accordingly, suitable means as well known in the art may be provided for introducing the liquid or gaseous form of the alkoxylating agent into the column. Carrier gases may also be used to introduce the alcohol into the column especially in the vapor form.

As indicated above, the column can be any type of material inert to the products and reactants, and can be provided with packings or inserts generally employed for fractionation in fractional distillation. No particular length is critical, and the upper limit of the column length is merely a question of economics. Since one of the advantages of the process of the present invention is the conservation of energy, and since the process of the present invention permits the separation of the high purity products in relatively short columns having a reflux ratio substantially less than the 100:1 ratio used to separate the corresponding halosilanes, relatively short columns utilizing minimal energy can be used in the process of the present invention.

The column is also equipped with at least one entry point or port or introduction point for feeding the halosilanes or a mixture of halosilanes into the upper section of the column. As explained above, the halosilanes can be liquids, vapors or gaseous in form and are preferably introduced into the packed column at the upper-most part of the upper section of the column, depending upon the boiling points of the halosilanes and the alcohol. In one preferred embodiment, the introductory point for the halosilanes is about 7 to about 8 cm from the top of the column. The halosilanes are introduced into the column is gaseous or vapor or liquid form, and they may be introduced into the column in conjunction with an inert solvent, such as, toluene. Generally the feed port for the alcohol is lower than the feed port in the column for the halosilane, but when the alcohol has a boiling point higher than the halosilanes, it is preferred to provide at least one alcohol feed port higher than the halosilane feed ports. For example, if isopropanol is used as the alkoxylating agent rather than methanol in the co-alkoxylation of methyltrichlorosilane and dimethyldichlorosilane, the isopropanol is preferably at a point higher in the column than the halosilanes.

The alkoxysilanes may be collected at any suitable point below the reaction zone of the heated column. Thus, the alkoxysilanes may be collected in the reboiler and separated by distillation. The alkoxysilanes may also be collected in the reboiler and subsequently pass to a receiver connected thereto and separated by distillation of other suitable means. In another embodiment, the alkoxysilanes may be collected at a point in the column below the reaction zone, for example, in a collection zone in the heated column, and separated by distillation or other suitable means. In the most preferred embodiment, and the embodiment preferred for continuous operation of the process, the alkoxysilanes are collected at a plurality of distillation points or collection ports in the column. Accordingly, when dimethyldimethoxysilane is separated from methyltrimethoxysilane, a point or port in the column at which dimethyldimethoxysilane distills, may be provided to remove the dimethyldimethoxysilane, and a point or port in the column at which methyltrimethoxysilane distills, may be provided to collect the methyltrimethoxysilane. Naturally, a plurality of the collection ports for collecting various alkoxysilanes may be utilized in the distillation section or portion of the column, and one skilled in the art can determine the optimum portion of the column to collect a particular fraction or alkoxysilane compound.

In certain embodiments the column is also heated by an external source of heat to provide maximum efficiency in the heating of any particular zone, and accordingly, the amount of heat applied to any particular zone can be regulated by providing modular heating zones upon the packed column. Thus, it is within the purview of one skilled in the art to choose appropriate temperatures at various points in the heated column, not only to maintain a suitable reaction temperature in the reaction zone, but also to achieve the desired distillation temperatures when the column is used to collect the alkoxysilane products formed from the respective halosilanes. Furthermore, the reboiler is provided with a source of heat so that temperatures approaching the reflux temperature of the components of the reboiler can be achieved.

In certain other embodiments, the column is insulated, and the temperature of the column is maintained by the heat of reaction and the heating of the reboiler.

In most preferred embodiments, the temperature of the heated column ranges from about 45° C. to about 70° C., depending upon the particular reaction ingredients including the particular alkoxylating agent. Generally, the temperature of the upper section of the column, that is, the reaction zone, is maintained at a temperature at least 0.5° C. above the boiling point of the particular alcohol used at the particular pressure prevailing in the column. In more preferred embodiments, the upper section of the column, that is, the reaction zone, is maintained at a temperature between about 48° C. and about 60° C.

When the heated column is used as a distillation column, and the alkoxysilanes, for example, methyltrimethoxysilane and dimethyldimethoxysilane, are collected therein and removed therefrom, the temperatures at the lower end of the column, that is, the end of the column proximal the reboiler, are maintained between about 61° C. to about 69° C., again depending upon the particular reaction products, that is, the particular alkoxysilanes being collected and separated therein. The reboiler is generally maintained at a temperature of about 70° C. to about 80° C. when methanol is used as the alkoxylating agent, however, generally, the reboiler is maintained at a temperature sufficient to maintain reflux conditions in the heated column. The temperature of the reboiler is dependent upon the components used therein, especially the boiling point of the alcohol and/or other components used therein.

When dimethyldimethoxysilane is collected at a collection point in the column, the temperature of the column at the collection and separation point, that is, in the distillation zone of the heated column, is maintained at about 61° C. to about 68° C. At the point where the methyltrimethoxysilane is collected and separated at the distillation point in the column, the column is heated at a temperature of about 62° C. to about 69° C. One skilled in the art can determine the most efficient temperatures for collecting and separating specific alkoxysilanes in the particular heated column at any set of given conditions. Naturally, the distance of the collection and separation point, as well as the length of the reaction zone, can be optimized, and positions of entry ports and collection and separation ports not only depend upon the particular reactants and products being formed and separated but also upon the length of the column, the pressure of the column, the number of reactants and products, the characteristics of adjuvants, and the like.

Generally, at the start up of the process, the reboiler is charged at least with the alkoxylating agent which is heated to reflux, and thereby provides an excess of the gaseous alkoxylating agent at the head, that is, in the upper section of, the column. Optionally, the halosilanes being converted to alkoxysilanes and/or the alkoxysilanes can also be incorporated into the reboiler at start up. At start up, the heating of the reboiler containing at least one of the compounds selected from the group consisting of the alkoxylating agent, the halosilanes being alkoxylated and separated, and the corresponding alkoxysilanes being formed, establishes a steady state in the column and thereby tends to optimize the production of the alkoxysilanes. In preferred embodiments, the reboiler contains the alcohol and the halosilane mixture at start up. For example, in one preferred embodiment of the present invention, the reboiler contains methanol, methyltrichlorosilane and dimethyldichlorosilane in approximately 1:1 equimolar quantities of alcohol to halosilanes at start up to provide optimum conditions under reflux in the column for the preparation of the respective alkoxysilanes. In certain cases, the use of only the alcohol in the reboiler may lead to the production of undesirable side products in the alkoxysilanes.

The following examples are given for the purpose of illustrating the invention and are not given for the purpose of limiting the definition of the invention as set forth in the instant specification.

EXAMPLES

A glass column having a 2.54 cm. (1 inch) internal diameter and a length of 122 cm. (4 feet) was packed with 4 mm×4 mm ceramic saddles. The methoxylation reactor was equipped with several feed ports, a chlorosilane feed port located 7.6 cm. (3 inches) from the top of the column, and four methanol feed ports located respectively 7.6 cm. (3 inches), 38.1 cm. (15 inches), 61 cm. (24 inches) and 91.4 cm. (36 inches) from the top of the column. Connected to the top of a column was a condenser which, during operation, was maintained at about −10° C. to about −20° C. by a circulating refrigerated methanol and a hydrogen chloride scrubber. Connected to the bottom of the column was a 1-liter reboiler provided with a continuous take-off system and a receiver.

EXAMPLES 1-6

The reactor was started by charging the reboiler with a solution containing 5 weight percent methanol, 80 weight percent dimethyldichlorosilane and 15 weight percent methyltrichlorosilane and heating it to reflux into the column. A chlorosilane feed mixture was fed into the feed port described above at 7.6 cm. from the top of the column, and methanol was fed simultaneously through the feed ports located at 7.6 cm., 38.1 cm., 61 cm. and 91.4 cm. from the top of the column. The chlorosilane feed was a mixture of 83 weight percent dimethyldichlorosilane and 17 weight percent methyltrichlorosilane. Steady state was reached in about one hour during sustained six-hour runs. The results of the several examples each representing a six-hour run, are given in the following table where varous chlorosilanes/methanol feed rates in grams per hour; chlorosilane/methanol feed locations per each sample are given; and the products isolated and identified by gas chromatographic analysis are shown for each example.

121.9 cm. (4 feet) from the top of the column, and a temperature indicator was provided at the reboiler. A condenser maintained at −10° C. to −20° C. by a circulating refrigerated methanol was connected to the top of the column. A 1-liter reboiler was used at the bottom of the column, and a continuous product take-off receiver was attached and connected to the reboiler.

A solution containing 5 weight percent methanol, 85 weight percent dimethyldichlorosilane and 15 weight percent methyltrichlorosilane, a total of 100 ml. of solution, was charged to the reboiler and heated to reflux into the column. Liquid chlorosilane containing about 83 weight percent dimethyldichlorosilane and 17 weight percent methyltrichlorosilane were fed into the column simultaneously with methanol. In determining the preferred mode of operation for the particular column and the particular mixture of ingredients, it was found that the methanol feed stream produced best results when located at the 38.1 cm. location, or alternatively expressed, at a point 30.5 cm. (1 foot) below the chlorosilane mixture feed stream. Temperatures between 55° C. to 61° C. and from 62° C. to 65° C. were established in the top one-half of the column and bottom one-half of the column respectively, while a temperature of between 70° and 75° C. prevailed in the reboiler. Hydrogen chloride was collected in a water trap.

It can be seen from the foregoing examples, that temperature conditions vary within the column, and that various combinations of products are obtained depending upon the particular variables such as feed rates of chlorosilane/methanol and feed location such as the location of the stream of methanol relative to the stream of the chlorosilanes.

While other modifications of the invention and variations thereof which may be employed within the scope of the invention, have not been described, the invention is intended to include such modifications as may be embraced within the following claims.

TABLE

|  | Examples | | | | | |
|---|---|---|---|---|---|---|
|  | 1 | 2 | 3 | 4 | 5 | 6 |
| —SiCl to methanol mole Ratio | 1:1 | 1:1 | 1:1.09 | 1:1 | 1:1.05 | 1:1.05 |
| Chlorosilane/Methanol feed rates, g/hr. | 65/34 | 65/34 | 63/36 | 91/48 | 90/49 | 69/36 vaporized*4. MeOH |
| Chlorosilane/Methanol feed location* | 3"/3" | 3"/15" | 3"/15" | 3"/24" | 3"/36" | 3"/36" |
| Yield* (%) | 91 | 89 | 91 | 92 | 91 | 91 |
| % Hydrolyzable Chloride | 3.0 | 1.7 | 2.0 | 2.9 | 1.8 | 2.2 |
| PRODUCT COMPOSITION (GC ANALYSIS) | | | | | | |
| *MeOH (%) | 9 | 12 | 15 | 5 | 9 | 10 |
| Me$_2$Si(OMe)Cl (%) | 6 | 3 | 2.6 | 7 | 6 | 5 |
| Me$_2$Si(OMe)$_2$ (%) | 65 | 64 | 61 | 67 | 63 | 65 |
| MeSi(OMe)$_2$Cl (%) | 0.2 | 0.1 | 0.2 | 0.4 | 0.3 | 0.3 |
| MeSi(OMe)$_3$ (%) | 13 | 12 | 14 | 17 | 16 | 14 |
| High Boilers (%) | 6.8 | 8.9 | 7.2 | 3.6 | 5.7 | 5.7 |

*1. Feed location measured from top of column.
*2. Yield is based on the amount of —SiCl converted to —SiOMe monomers
*3. Me represents methyl
*4. Methanol was preheated and fed as a vapor into the column.

EXAMPLE 7

A reactor similar to that described above having two feed ports each at the 7.6 cm. (3 inch), 38.1 cm. (15 inches), 61 cm. (24 inches) and 91.4 cm. (36 inches) as measured from the top of the column, was used in this example. Temperature indicators were also provided at 30.48 cm. (1 foot), 61 cm. (2 feet), 91.4 cm (3 feet) and

What is claimed is:

1. A process for converting a mixture of at least two different halosilanes having the general formula, $R_nSiX_{4-n}$ to at least two different alkoxysilanes having the formula, $R_nSi(OR')_{4-n}$, where R and R' are selected from the group consisting of saturated or unsaturated alkyl radicals of 1 to about 8 carbon atoms, substituted saturated or unsaturated alkyl radicals of 1 to about 8 carbon atoms, cyclic carbon groups of about 4 to about 10 carbon atoms, substituted cyclic carbon groups of about 4 to about 10 carbon atoms, and except for R', hydrogen; X is halogen; and n is 0 to 3; and separating the alkoxysilanes, comprising:

(a) charging a reboiler equipped with a column with at least one compound selected from the group consisting of an alcohol having the formula, R'OH, and, optionally, at least one halosilane having the formula, $R_nSiX_{4-n}$, or the corresponding alkoxysilane having the formula $R_nSi(OR')_{4-n}$; where R and R' are selected from the group consisting of saturated or unsaturated alkyl radicals of 1 to about 8 carbon atoms, substituted saturated or unsaturated alkyl radicals of 1 to about 8 carbon atoms, cyclic carbon groups of about 4 to about 10 carbon atoms, substituted cyclic carbon groups of about 4 to about 10 carbon atoms, and except for R', hydrogen; X is halogen; and n is 1 to 3; the lower end of the column being connected to the reboiler;

(b) heating the reboiler at a temperature to cause the contents of the reboiler to reflux in the column;

(c) feeding at least two halosilanes having the formula, $R_nSiX_{4-n}$, where R, X and n are defined above, into the column;

(d) introducing an alcohol having the formula, R'OH, where R' is defined above, into the column at a point wherein the alcohol passes into a reaction zone in the column, and the alcohol and the halosilanes react in the reaction zone to form the corresponding alkoxysilanes and hydrogen chloride;

(e) removing the hydrogen chloride;

(f) collecting at least two alkoxysilanes; and (g) separating the alkoxysilanes.

2. The process of claim 1 comprising continuously feeding a mixture of two halosilanes and the alcohol into the column.

3. The process of claims 1 or 2 comprising introducing the alcohol into the column at a point in the heated column below the halosilanes.

4. The process of claims 1 or 2 comprising introducing the alcohol into the column at a point in the column near the point of introduction of the halosilanes.

5. The process of claims 1 or 2 comprising introducing the alcohol into the column at a point in the column above the halosilanes.

6. The process of claims 1 or 2 comprising introducing the alcohol into the column at a plurality of points along the length of the column.

7. The process of claims 1 or 2 comprising introducing the halosilanes into the column at a plurality of points along the length of the column.

8. The process of claims 1 or 2 comprising introducing the alcohol into the heated column at a plurality of points along the length of the column wherein one of the plurality of alcohol introduction points is at about the level of the introduction of the halosilanes and at least one of the plurality of alcohol introduction points is below the level of the introduction of the halosilanes.

9. The process of claims 1 or 2 comprising collecting the alkoxysilanes in the reboiler and separating the alkoxysilanes by distillation.

10. The process of claims 1 or 2 comprising collecting the alkoxysilanes in a receiver connected to the reboiler and separating the alkoxysilanes by distillation.

11. The process of claims 1 or 2 comprising collecting the alkoxysilanes at a point in the column below the reaction zone and separating the alkoxysilanes by distillation.

12. The process of claims 1 or 2 comprising collecting the at least two different alkoxysilanes at a plurality of distillation points in the column.

13. The process of claim 1 further comprising heating the column to maintain a temperature in the column sufficient to cause a reaction between the alcohol and the halosilanes.

14. The process of claims 1 or 2 further comprising heating the column to maintain a temperature sufficient to cause the separation of the alkoxysilanes in a distillation zone.

15. The process of claims 1, 2 or 13 wherein the temperature of the heated column is about 45° C. to about 70° C.

16. The process of claims 1, 2 or 13 wherein the temperature in the reaction zone of the column is about 48° C. to about 60° C.

17. The process of claims 1 or 2 wherein the temperature in the column at a point below the reaction zone is about 61° C. to about 69° C.

18. The process of claims 1 or 2 wherein the temperature of the reboiler is about 70° C. to about 80° C.

19. The process of claims 1 or 2 wherein the section of the column below the reaction zone is a distillation zone in which the at least two alkoxysilanes are separated and collected, and the temperature of the distillation zone varies between about 60° C. to about 70° C.

20. The process of claims 1 or 2 wherein R and R' are selected from the group consisting of methyl, ethyl, n-propyl, iso-propyl, n-butyl, iso-butyl, phenyl, tolyl, vinyl and allyl, and X is chlorine.

21. The process of claims 1 or 2 wherein the alcohol is an aliphatic alcohol.

22. The process of claims 1 or 2 wherein the alcohol is methanol.

23. The process of claims 1 or 2 further comprising separating the alkoxysilanes by distillation.

24. A process for converting a mixture of dimethyldichlorosilane and methyltrichlorosilane which are difficult to separate, to dimethyldimethoxysilane and methyltrimethoxysilane by the co-methoxylation of the dimethyldichlorosilane and methyltrichlorosilane and separating the dimethyldimethoxysilane and methyltrimethoxysilane, comprising:

(a) feeding a stream of dimethyldichlorosilane and methyltrichlorosilane into a column connected to a reboiler;

(b) continuously introducing methanol into the colum simultaneously with the stream of dimethyldichlorosilane and methyltrichlorosilane at a point wherein the methanol passes into a reaction zone in the column whereby the methanol reacts with the dimethyldichlorosilane and methyltrichlorosilane to form dimethyldimethoxysilane, methyltrimethoxysilane and hydrogen chloride in the column;

(c) heating a reboiler charged with at least one compound selected from the group consisting of methanol, dimethyldichlorosilane, dimethyldimethoxysilane, methyltrimethoxysilane and methyltrichlorosilane, to pass the at least one compound into the column;

(d) removing hydrogen chloride from the top of the column;

(e) collecting the dimethyldimethoxysilane and methyltrimethoxysilane below the reaction zone; and (f) separating the dimethyldimethoxysilane from the methyltrimethoxysilane.

25. The process of claim 24 comprising continuously feeding a mixture of the dimethyldichlorosilane and the methyltrichlorosilane into the column.

26. The process of claim 24 comprising continuously introducing the methanol into the column at a point in the column below the dimethyldichlorosilane and the methyltrichlorosilane.

27. The process of claim 24 comprising continuously introducing the methanol in the column at a point in the column near the point of introduction of the dimethyldichlorosilane and the methyltrichlorosilane.

28. The process of claim 24 comprising continuously introducing the methanol into the column at a plurality of points in the column.

29. The process of claim 24 comprising continuously introducing the dimethyldichlorosilane and methyltrichlorosilane into the column at a plurality of points in the column.

30. The process of claim 24 comprising continuously introducing the methanol into the column both at a point in the column below the dimethyldichlorosilane and the methyltrichlorosilane and at a point in the column near the dimethyldichlorosilane and the methyltrichlorosilane.

31. The process of claim 24 comprising collecting the dimethyldimethoxysilane and methyltrimethoxysilane in the reboiler and separating the dimethyldimethoxysilane from the methyltrimethoxysilane by distillation.

32. The process of claim 24 further comprising collecting the dimethyldimethoxysilane and methyltrimethoxysilane in a receiver connected to the reboiler and separating the dimethyldimethoxysilane from the methyltrimethoxysilane by distillation.

33. The process of claim 24 further comprising collecting the dimethyldimethoxysilane at a distillation point in the column below the reaction zone in the column.

34. The process of claim 24 further comprising collecting the methyltrimethoxysilane at a distillation point in the column below the reaction zone in the column.

35. The process of claims 24, 33 or 34 further comprising collecting the methyltrimethoxysilane at a distillation point in the column below a distillation point in the column wherein dimethyldimethoxysilane is collected.

36. The process of claim 24 further comprising heating the column to maintain a temperature in the column sufficient to cause a reaction between the methanol and the dimethyldichlorosilane and the methyltrichlorosilane.

37. The process of claim 24 further comprising heating the column to maintain a temperature in the column sufficient to cause the separation of the dimethyldimethoxysilane and the methyltrimethoxysilane in a distillation zone.

38. The process of claims 24, 36 or 37 wherein the temperature of the heated column is about 45° C. to 70° C.

39. The process of claims 24 or 36 wherein the temperature of the reaction zone of the column is about 48° C. to about 60° C.

40. The process of claims 24, 36 or 37 wherein the temperature of the column at a point below the reaction zone is about 61° C. to about 69° C.

41. The process of claim 24 wherein the reboiler is heated at about 70° C. to about 80° C.

42. The process of claims 33, 34 or 37 wherein the column is heated at a temperature of between about 62° C. to about 65° C. at the distillation point.

43. The process of claim 33 wherein the column is heated at a temperature of about 61° C. to about 68° C. at the distillation point in the column wherein the dimethyldimethoxysilane is collected.

44. The process of claim 34 wherein the column is heated at a temperature of about 62° C. to about 69° C. at the distillation point in the column wherein the methyltrimethoxysilane is collected.

* * * * *